United States Patent
Fackelmeier

(10) Patent No.: US 10,520,565 B2
(45) Date of Patent: Dec. 31, 2019

(54) COUPLER FOR SIGNAL TRANSMISSION

(71) Applicant: Siemens Healthcare GmbH, Erlangen (DE)

(72) Inventor: Andreas Fackelmeier, Thalmaessing (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 0 days.

(21) Appl. No.: 15/992,280

(22) Filed: May 30, 2018

(65) Prior Publication Data
US 2018/0348317 A1 Dec. 6, 2018

(30) Foreign Application Priority Data

Jun. 2, 2017 (EP) .................................. 17174216

(51) Int. Cl.
*G01R 33/36* (2006.01)
*G01R 33/341* (2006.01)
(Continued)

(52) U.S. Cl.
CPC .......... *G01R 33/3692* (2013.01); *B60L 53/34* (2019.02); *G01R 33/341* (2013.01);
(Continued)

(58) Field of Classification Search
CPC ............. G01R 33/3692; G01R 33/341; G01R 33/3642; G01R 33/34007; H01F 38/14;
(Continued)

(56) References Cited

U.S. PATENT DOCUMENTS

| 4,527,163 A | 7/1985 | Stanton |
| 6,908,960 B2 * | 6/2005 | Takaya ................ H01B 3/442 428/432 |

(Continued)

FOREIGN PATENT DOCUMENTS

| CN | 101053113 A | 10/2007 |
| CN | 106532970 A | 3/2017 |
| WO | WO-2009069097 | 6/2009 |

OTHER PUBLICATIONS

Extended European Search Report and English translation thereof dated Nov. 21, 2017.
(Continued)

*Primary Examiner* — Dixomara Vargas
(74) *Attorney, Agent, or Firm* — Harness, Dickey & Pierce, P.L.C.

(57) ABSTRACT

A coupler includes a first and second coupler element, with a respective first and second transmission element. In an embodiment, a first signal contact for connection to a signal conductor is arranged on a first end of the first transmission element; a second signal contact for connection to a signal conductor is arranged on a first end of the second transmission element; the first transmission element forms a plurality of first U-shaped curves between the first end and a second end; and the second transmission element forms a plurality of second U-shaped curves between the first end and a second end. The first transmission element is configured, in operation, to transmit a signal supplied at the first signal contact to the second transmission element via directional coupling and the second transmission element is configured, in operation, to receive and output the signal via the second signal contact.

12 Claims, 3 Drawing Sheets

(51) Int. Cl.
    *H01F 38/14*     (2006.01)
    *H01Q 1/27*      (2006.01)
    *H04B 5/00*      (2006.01)
    *G01R 33/34*     (2006.01)
    *B60L 53/34*     (2019.01)
    *A61B 6/00*      (2006.01)
    *H01Q 1/36*      (2006.01)
    *H01Q 9/42*      (2006.01)
    *H05K 1/16*      (2006.01)
    *H01Q 5/40*      (2015.01)

(52) U.S. Cl.
    CPC ... *G01R 33/34007* (2013.01); *G01R 33/3642* (2013.01); *H01F 38/14* (2013.01); *H01Q 1/273* (2013.01); *H04B 5/0031* (2013.01); *H04B 5/0037* (2013.01); *H04B 5/0081* (2013.01); *H04B 5/0093* (2013.01); *A61B 6/56* (2013.01); *H01Q 1/36* (2013.01); *H01Q 5/40* (2015.01); *H01Q 9/42* (2013.01); *H05K 1/165* (2013.01); *H05K 2201/09263* (2013.01); *H05K 2201/10098* (2013.01); *Y02T 10/7088* (2013.01); *Y02T 90/122* (2013.01)

(58) Field of Classification Search
    CPC .... H01Q 1/273; H04B 5/0037; H04B 5/0093; H04B 5/0081; B60L 53/34
    See application file for complete search history.

(56) References Cited

U.S. PATENT DOCUMENTS

| | | | | |
|---|---|---|---|---|
| 2002/0132898 | A1* | 9/2002 | Takaya | H01B 3/442 524/445 |
| 2003/0030994 | A1* | 2/2003 | Takaya | H01F 5/06 361/728 |
| 2005/0003199 | A1* | 1/2005 | Takaya | B32B 15/08 428/413 |
| 2005/0130446 | A1* | 6/2005 | Takaya | H01B 3/442 438/780 |
| 2005/0130447 | A1* | 6/2005 | Takaya | H01B 3/442 438/780 |
| 2005/0154110 | A1* | 7/2005 | Takaya | H01B 3/442 524/413 |
| 2007/0040627 | A1 | 2/2007 | Kanno et al. | |
| 2008/0044660 | A1* | 2/2008 | Takaya | B32B 15/08 428/413 |
| 2012/0067872 | A1* | 3/2012 | Libman | H05B 6/647 219/702 |
| 2012/0326520 | A1 | 12/2012 | Konya | |
| 2016/0020508 | A1 | 1/2016 | Alexopoulos et al. | |
| 2018/0214204 | A1* | 8/2018 | Karmarkar | A61B 5/05 |

OTHER PUBLICATIONS

European Office Action and English translation thereof dated May 3, 2018.
European Intention to Grant and English translation thereof dated Jan. 29, 2019.
German Office Action dated Nov. 21, 2017.
Debatosh Guha et al: "Microstrip and Printed Antennas—New Trends, Techniques and Applications"; In: "Microstrip and Printed Antennas—New Trends, Techniques and Applications"; John Wiley & Sons Inc, New York; NY; US; XP055337090; ISBN: 978-0-470-68192-3; pp. 1-253.
Chinese Office Action and partial English translation dated Jul. 2, 2019.

* cited by examiner

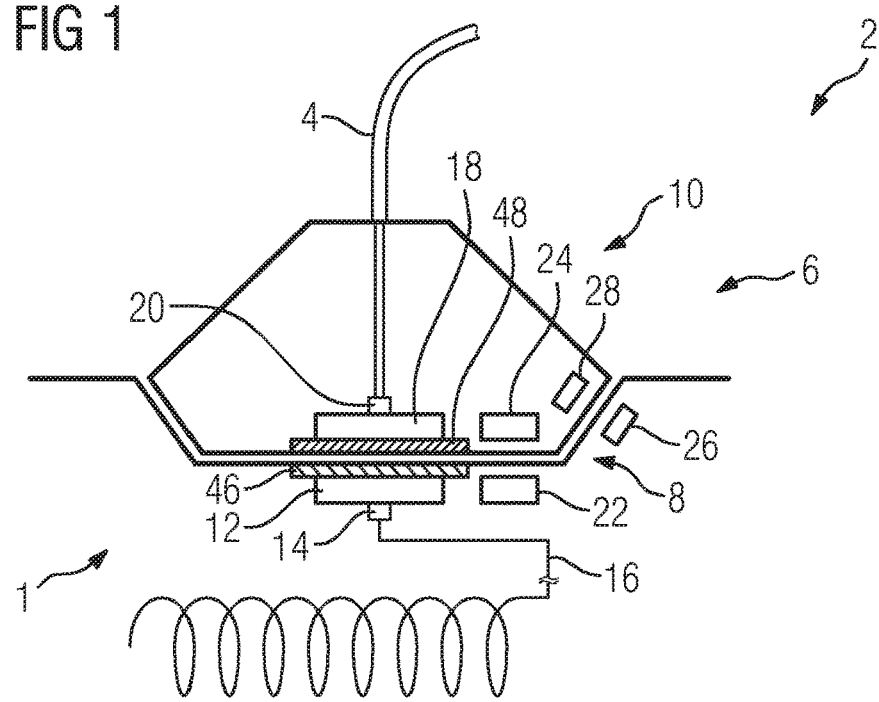
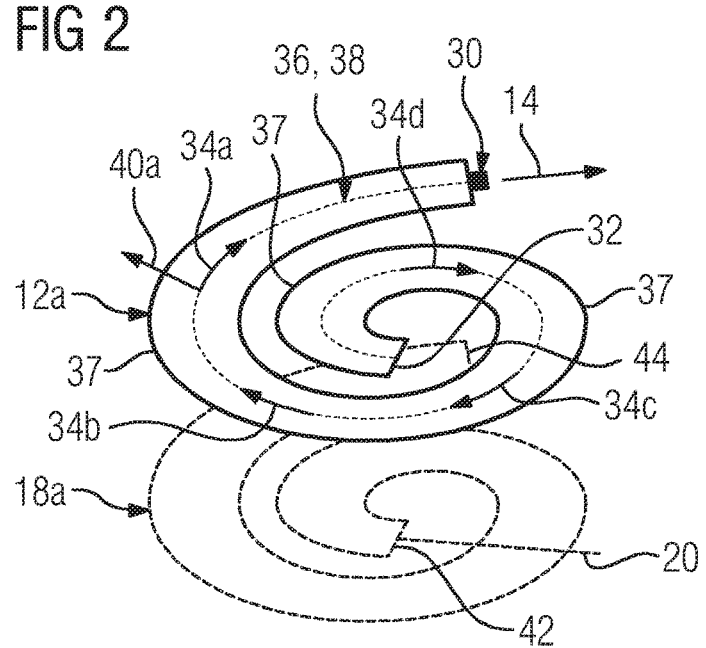

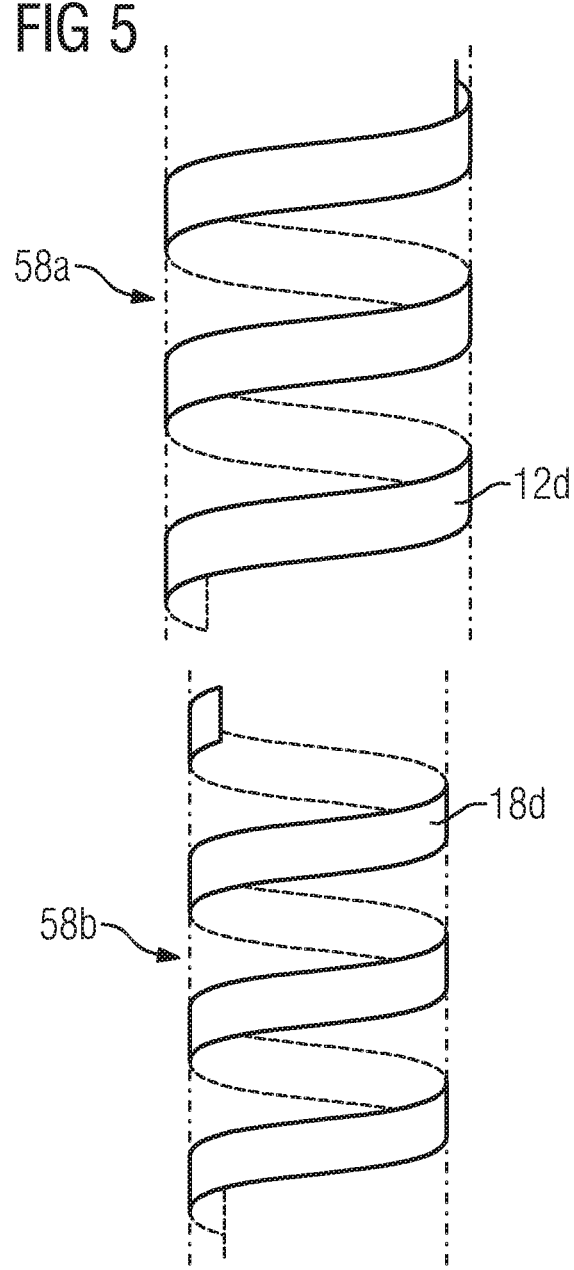

US 10,520,565 B2

COUPLER FOR SIGNAL TRANSMISSION

PRIORITY STATEMENT

The present application hereby claims priority under 35 U.S.C. § 119 to European patent application number EP 17174216.6 filed Jun. 2, 2017, the entire contents of which are hereby incorporated herein by reference.

FIELD

At least one embodiment of the invention generally relates to a coupler for signal transmission comprising a first coupler element with a first transmission element and a second coupler element with a second transmission element, wherein a first signal contact for connection to a signal conductor is arranged on a first end of the first transmission element, wherein a second signal contact for connection to a signal conductor is arranged on a first end of the second transmission element, wherein the first transmission element is configured, in operation, to transmit a signal supplied at the first signal contact to the second transmission element and wherein the second transmission element is configured, in operation, to receive the signal from the first transmission element and output it via the second signal contact.

BACKGROUND

In many different applications, in the case of data generation during a technical procedure, there is a requirement to transmit the generated data with the highest possible data rate from a data-generating component of a device to a data-processing component of the device that is physically separate from the data-generating component. This requirement occurs in many technical fields independently of the type of data generation and independently of the type and also the purpose of the further processing of the data. Herein, in many cases, the implementation of the data transmission is fully coordinated with the higher-ranking technical process, i.e. an independent technical solution for data transmission is developed, in particular if it is necessary to cope with particularly high data rates and preprocessing of the data, which is generally necessary for embedding in standardized transmission protocols, is not desirable or quite simply unfeasible during the data generation.

This scenario is encountered particularly frequently in medical imaging where comparatively large volumes of image data are generated in a very short time and have to be transmitted from, frequently moving, parts of devices to a computing unit that executes the corresponding reconstruction algorithms. The trend toward ever higher image resolution with each individual image generated due to the growing physical possibilities of imaging and toward a shortest possible sequence of individual images in order to avoid falsification due to body movements, intensify the requirements on said data transmission. For example, in the case of magnetic resonance imaging (MRI) there is a need to transmit proprietary data signals from a local coil to a patient's bench. A further example of a transmission process entails the receive signals generated in a transducer for an ultrasound device.

Due to the large volumes of data to be transmitted, such applications frequently require the use of expensive, bulky connectors and correspondingly thick cables. Such connectors and cables have drawbacks when used with medical imaging devices as they are inconvenient to handle and very heavy. For example, the high weight of the transmission cables used means that a local coil for MRI has to have additional fastening to ensure it is not displaced by the cable. In addition, the connectors used frequently have numerous contacts since it is necessary to transmit a very high number of individual channels and the contacts are often difficult to clean and, in addition, are frequently not capable of a high number of mating cycles. Herein, it is in particular necessary to note that, even if redundancy channels are provided in the transmission protocol, a connector may be no longer able to provide reliable data transmission in the event of a few faulty contacts.

Herein, the requirements named are not restricted to connectors as transmission device(s) but can also extend to virtually every type of coupler for signal transmission with high data rates.

SUMMARY

At least one embodiment of the invention is directed to a coupler for signal transmission with the highest possible data rate, coupling that is robust as possible with respect to mechanical tolerances and a design that is as compact as possible.

At least one embodiment of the invention is directed to a coupler for contactless signal transmission comprising a first coupler element with a first transmission element and a second coupler element with a second transmission element, wherein a first signal contact for connection to a signal conductor is arranged on a first end of the first transmission element, wherein a second signal contact for connection to a signal conductor is arranged on a first end of the second transmission element, wherein the first transmission element forms a plurality of first U-shaped curves between the first end and a second end, wherein the second transmission element forms a plurality of second U-shaped curves between the first end and a second end, wherein the first transmission element is configured, in operation, to transmit a signal supplied at the first signal contact to the second transmission element by way of directional coupling and wherein the second transmission element is configured, in operation, to receive the signal from the first transmission element and output it via the second signal contact.

At least one embodiment of the invention further discloses a magnetic resonance imaging system with a local coil and a coupler of at least one embodiment as described above, wherein the first coupler element of the coupler is arranged on the local coil. Herein, the advantages disclosed for at least one embodiment of coupler and the developments thereof can be transferred analogously to the magnetic resonance imaging system.

BRIEF DESCRIPTION OF THE DRAWINGS

The following describes an example embodiment of the invention with reference to a drawing, which shows, schematically in each case:

FIG. 1 a sectional view of a local coil of an MRI system with a coupler,

FIG. 2 a perspective view of two planar spiral-shaped transmission elements of a coupler as shown in FIG. 1, FIG. 3 in a perspective view of two planar meander-shaped transmission elements of a coupler as shown in FIG. 1, FIG. 4 a side view of two spiral-shaped transmission elements of a coupler, which each extend along cone surfaces and FIG. 5 a side view of two transmission elements of a coupler, which each extend along cylinder surfaces.

Parts and sizes corresponding to one another are in each case given the same reference numbers in all the figures.

DETAILED DESCRIPTION OF THE EXAMPLE EMBODIMENTS

Figure 3:
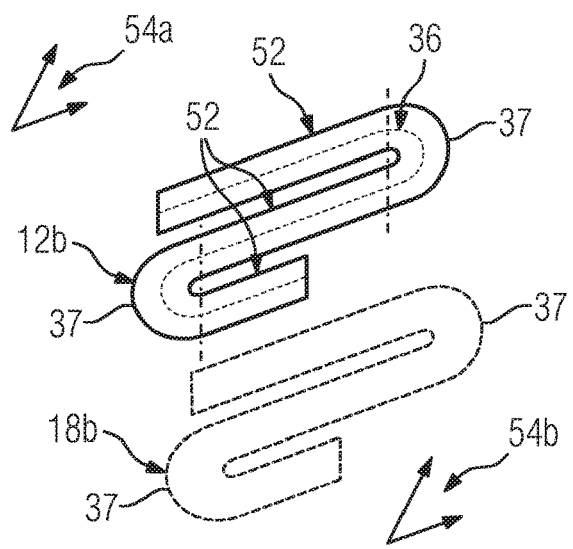

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a coupler for contactless signal transmission comprising a first coupler element with a first transmission element and a second coupler element with a second transmission element, wherein a first signal contact for connection to a signal conductor is arranged on a first end of the first transmission element, wherein a second signal contact for connection to a signal conductor is arranged on a first end of the second transmission element, wherein the first transmission element forms a plurality of first U-shaped curves between the first end and a second end, wherein the second transmission element forms a plurality of second U-shaped curves between the first end and a second end, wherein the first transmission element is configured, in operation, to transmit a signal supplied at the first signal contact to the second transmission element by way of directional coupling and wherein the second transmission element is configured, in operation, to receive the signal from the first transmission element and output it via the second signal contact.

Advantageous and partly per se inventive embodiments are set out in the claims and in the following description.

The coupler can, in at least one embodiment, be configured for bidirectional signal transmission so that the second transmission element is configured, in operation, to transmit a signal supplied at the second signal contact to the first transmission element by way of directional coupling and the first transmission element is configured, in operation, to receive the signal from the second transmission element and output it via the first signal contact.

Herein, a coupler generally refers to a two-element apparatus, which is configured, in operation, to transmit a signal between the two elements, wherein the two elements are embodied to be reversibly detachable from one another. The first transmission element and the second transmission element are, in at least one embodiment, preferably each embodied such that a preferred direction can be defined locally so that directional coupling takes place locally with respect to this preferred direction, which also determines the signal path within the respective transmission element. The local preferred directions then extend in each case from the signal contact arranged at the first end of the respective transmission element along the transmission element as far as the second end.

Here, a U-shaped curve generally refers to any curvature of the respective transmission element about 180°, i.e. in particular also a curve without any straight incoming or outgoing sections toward or away from the actual curvature. Herein, the formation of a plurality of U-shaped curves by one of the two transmission elements between its first end and its second end should in particular be understood to mean that the totality of the local preferred directions of the respective transmission element between the first end and the second end defines a line profile, wherein the lines could, for example, be defined by the local boundaries of the transmission element in a spatial direction that is locally perpendicular to the preferred direction and that the line profile includes the corresponding U-shaped curves.

Herein, on the one hand, the plurality of U-shaped curves can always have the same direction of curvature, as is the case, for example, with a spiral, or, on the other, the direction of curvature can also alternate thus forming a meandering line profile. Herein, it is in particular possible for individual U-shaped curves to be separated from one another by straight sections in the line profile of the respective transmission element and in particular it is also possible for individual U-shaped curves between an input point and an output point of the respective curve to have a number of straight sections without any curvature of the preferred direction or the line path so that the entire curvature between the input point and the output point adds up to 180°.

It is also possible for a transmission element to have no straight sections in its line profile but to be formed from a continuous string of U-shaped curves, which in turn each have constant curvature. This is, for example, the case with a transmission element embodied as a spiral or with a transmission element wound up along a cone surface or a transmission element wound around a cylinder surface. Particularly preferably, herein the spatial orientation of the second U-shaped curves of the second transmission element emulates the first U-shaped curves of the first transmission element.

Herein, directional coupling should in particular be understood to be the mutual crosstalk of two electrical conductors which are located in the immediate vicinity of one another but are not in conductive contact with one another. The use of a directional coupling of this kind in the coupler according to the invention enables physical contact between the first transmission element and the second transmission element to be dispensed with. With such physical contact, depending on the type of data transmission and possibly the transmission protocol, it is often necessary to contact a plurality of individual transmission channels on the first transmission element and on the second transmission element of a coupler according to the prior art separately. This results in either disadvantageous dimensioning of the corresponding coupler or particularly small points of contact which, in the case of frequent separation of the two coupler elements from one another, could easily become worn as a result of the physical contact.

Herein, directional couplers such as those used in radio-frequency engineering generally use two planar strip-shaped conductors as transmission elements, wherein the effective length of the signal transmission line for both conductors is typically a quarter of the wavelength of the signal to be transmitted. Even if herein some structural configurations, relating, for example, to the spacing of the two conductors during transmission or the use of dielectric substrates between the two conductors provide some leeway, this does not affect the basic length of the transmission line.

However, for many applications, in particular those in which the two couplers have to be separated from one another more frequently, i.e. inter alia including the field of medical imaging, planar strip conductors are impractical as transmission elements due to the complicated positioning with respect to one another as a result of the high sensitivity to mechanical tolerances and the relative length of the transmission line. This problem when using directional couplers is now resolved by the invention in that the first transmission element and the second transmission element are "wound up" over the respective U-shaped curves, so that, on the one hand, the space requirement can be greatly reduced and, on the other, the positioning of the two transmission elements relative to one another is much less complicated due to much greater robustness with respect to deviations.

Due to the fact that the two transmission elements actually each acquire a flat extension from the U-shaped curves, to utilize the directional coupler effect, it is now no longer necessary to position two strip-shaped conductors relative to one another but instead essentially two surfaces are to be aligned with one other, which frequently produces a much simpler design. Herein, the attachment of the first coupler element to the second coupler element for the operation of the coupler can be designed as completely separate from the signal transmission and possibly, in the case of wear, also replaced separately therefrom thus additionally increasing the lifetime of the coupler.

Herein, the first transmission element and the second transmission element preferably, in at least one embodiment, each lie in one plane or the first transmission element and the second transmission element extend along surfaces of revolution, which are mutually complementary. Herein, a surface of revolution is a surface formed by rotating a planar curve about an axis of rotation lying in the same plane. Therefore, this in particular also includes a cylinder surface. Advantageously, herein the surface of revolution extends in a direction of the axis of rotation with a monotonic increase in the distance from the axis of rotation. The described extension in each case in one plane or along complementary surfaces of revolution enables the first transmission element and the second transmission element to be aligned with one another in a particularly simple manner, wherein the extension along complementary surfaces of revolution can additionally ensure that, in operation, the first transmission element and the second transmission element are at a short distance from another, at least in sections, and this is advantageous for contactless transmission.

The intrinsic rotational symmetry of the two planes or the rotational symmetry of the two mutually complementary surfaces of revolution also enables the first transmission element and the second transmission element each to be embodied such that rotations with respect to a common axis of symmetry only has a limited impact on the coupling strength of the directional coupling. This is particularly advantageous for the positioning of the first coupler element relative to the second coupler element.

Herein, expediently, the first coupler element is embodied as rotationally symmetrical and the second coupler element as complementary to the first coupler element. Preferably, herein a rotationally symmetrical shape of the first coupler element is defined by a corresponding surface in which the first transmission element extends. The rotational symmetry and the complementary embodiment enable the first coupler element and the second coupler element to be connected mechanically to one another in a particularly simple manner.

Conveniently, the first transmission element forms a spiral between the first end and the second end. In particular, herein the spiral extends in a plane or along a cone surface. The second transmission element preferably forms a spiral between its first end and its second end, which particularly preferably corresponds to the spiral of the first transmission element. Specifically with significant rotation of the first transmission element with respect to the second transmission element, such an embodiment can ensure a high degree of spatial overlap with respect to the common spiral center and hence high coupling strength for the directional coupling.

In a further advantageous embodiment, the first transmission element is wound in a meandering pattern between the first end and the second end. Here, the second transmission element is also preferably wound in a meandering pattern between its first end and its second end, wherein particularly preferably the windings of the second transmission element correspond to the windings of the first transmission element. A meander-shaped embodiment of the transmission elements is in particular advantageous with a planar embodiment if, additionally, due to the structural design, there is an additional preferred direction in the respective plane of the coupling elements, i.e. for example in the case of substantially rectangular coupler elements. Herein, a meander-shaped embodiment of the respective transmission elements enables the available space to be better utilized.

It has also been found to be advantageous for the transmission element to be wound around a cylinder surface. Herein, the second transmission element is preferably wound about a lateral surface of the cylinder in a manner corresponding to the first transmission element. Such an embodiment enables the two transmission elements to take the shape of coaxial cylinders, wherein, for the operation of the coupler, a cylindrical coupler element is introduced into a corresponding cylindrical sleeve, which is formed by the other coupler element. When the two coupler elements are separated from one another this in particular means that the transmission element is particularly well protected against external influences in the cylindrical sleeve.

It has also been found to be advantageous, in at least one embodiment, for the first transmission element and/or the second transmission element, at least in sections, to be embodied locally in a flat shape. This in particular includes a strip-like embodiment. Herein, 'locally in a flat shape' should be understood to mean that there is local flattening in one direction perpendicular to the local preferred direction in the respective transmission element but widening in the other spatial direction perpendicular to the local preferred direction. Herein, in particular both the flattening and the widening are significant relative to the total cross-sectional area. This preferably produces locally a substantially rectangular or elliptical cross section the two spatial directions of which differ from one another by a least one order of magnitude. A local flatness of the first transmission element and/or of the second transmission element, at least in sections, enables an improvement to the coupling strength of directional coupling. In particular, the first transmission element and the second transmission element are each embodied as locally flat along their entire length, defined by the corresponding line path, between the first and second end.

The first transmission element, in at least one embodiment, is preferably applied to a dielectric substrate that forms a surface of the first coupler element. Particularly preferably, the second transmission element is also applied to a dielectric substrate that forms a surface of the second coupler element. Herein, it is in particular possible to use FR4 as a dielectric substrate.

In particular, in at least one embodiment, the dielectric substrate can be an electric insulator. The use of such a dielectric substrate, with which the first transmission element or the second transmission element covers the respective coupler element, makes it possible, for the operation of the coupler, to control the distance between the first transmission element and the second transmission element in a particularly simple manner. The two coupler elements are—preferably positively—brought into contact so that the dielectric substrate ensures that the two transmission elements have the correct spacing on the corresponding surfaces. This is in particular significant when considered against the background that, with directional couplers, the distance between the transmission elements has a decisive influence on the coupling strength and on the frequency response.

It has also been found to be advantageous, in at least one embodiment, for a first coil for inductive energy transmission to be arranged in the first coupler element and a second coil for inductive energy transmission to be arranged in the second coupler element, wherein the first coil and the second coil are configured, when the coupler is in operation, to transmit energy from the first coupler element to the second coupler element and/or from the second coupler element to the first coupler element. This means that the coupler can be used not only for signal transmission but also for energy transmission thus enabling a separate transmission line to be dispensed with in the higher-ranking application. This advantageously utilizes the circumstance that inductive energy transmission does not significantly interfere with the directional coupling used in the coupler for signal transmission.

Expediently in at least one embodiment, the first coupler element and the second coupler element each comprise an electromagnetic absorber. This is in particular advantageous if in each case at least one coil for inductive energy transmission is arranged in the first coupler element and in the second coupler element so that, when the coupler is in operation, inductive energy transmission taking place via the respective coils can be screened by the respective electromagnetic absorbers and hence does not interfere with the higher-ranking application.

The coupler, in at least one embodiment, is preferably configured for the transmission of signals in a frequency range of from 200 MHz to 4 GHz, particularly preferably in a frequency range of from 300 MHz to 2.5 GHz. Signal transmission by way of directional coupling in said frequency range requires effective coupling lengths, which can be in the range from centimeters to decimeters. With such effective coupling lengths, the suggested "winding-up" of the first transmission element and the second transmission element by way of corresponding U-shaped curves is particularly advantageous for the coupler dimensions.

At least one embodiment of the invention further discloses a magnetic resonance imaging system with a local coil and a coupler of at least one embodiment as described above, wherein the first coupler element of the coupler is arranged on the local coil. Herein, the advantages disclosed for at least one embodiment of coupler and the developments thereof can be transferred analogously to the magnetic resonance imaging system.

In FIG. 1 is a schematic sectional view of a local coil 1 of an MRI system 2 to which a reversibly separable data connection can be established via a cable 4 from a patient bench (not shown) of the MRI system 2 by a coupler 6. The coupler 6 comprises a first coupler element 8, which is arranged on the local coil 1 and a second coupler element 10, which is arranged on the end of the cable 4. The first coupler element 8 comprises a, still-to-be-described, first transmission element 12 with a first signal contact 14, which is in contact with a signal line 16 of the local coil 1. The second coupler element 10 comprises a, still-to-be-described, second transmission element 18 with a second signal contact 20, which is in contact with the end of the cable 4. The first coupler element 8 and the second coupler element 10 each further comprise a first coil 22 or a second coil 24 for an energy supply to the local coil 1 by way of inductive energy transmission and electromagnetic absorbers 26, 28 so that the inductive energy transmission interferes as little as possible with the overall operation of the MRI system 2. When the MRI system 2 is in operation, medical image data, which is generated in the local coil 1, is transmitted from the first transmission element 12 of the first coupler element 8 to the second transmission element 18 of the second coupler element 10 by way of directional coupling and the local coil is also supplied with power via the coils 22, 24.

FIG. 2 is a perspective view of the first transmission element 12a and the second transmission element 18a of the coupler 6 as shown in FIG. 1. The first signal contact 14 is arranged at a first end 30 of the first transmission element 12a. The first transmission element 12a extends in a spiral shape to its free second end 32. In particular, herein, it is possible in each case to define a preferred direction 34a-d locally, which is determined by the local signal course in the first transmission element 12a. Hence, the totality 36 of the local preferred directions 34a-d defines a line profile, which, in the present case, forms a plurality of concatenated U-shaped curves 37 with the same direction of curvature and hence a spiral 38. In a direction 40a perpendicular to the local preferred direction 34a, the first transmission element 12 has a significant spatial extension, wherein in the spatial direction (not shown) perpendicular to the direction 40a and to the local preferred direction 34a, the first transmission element 12a does not have any significant extension and hence forms a locally flat, strip-shaped structure.

The second transmission element 18a emulates, from its first end 42 to its free second end 44, the spiral shape of the first transmission element 12a. The second signal contact 20 with which the cable 4 is in contract is arranged at the first end 42. Both the first transmission element 12a and the second transmission element 18a are applied to a dielectric substrate 46, 48, which in each case forms the surface of the first or second coupler element 8, 10 in the common contact region.

The global spiral-shaped, but locally flat or strip-like embodiment of the first and second transmission element 12a, 18a on the one hand enables a much higher coupling strength to be achieved for the directional coupling than in the case of globally linear transmission elements with a length comparable to the diameter of the spiral. On the other hand, the transmission quality is robust with respect to rotation of the two transmission elements 12a, 18a in relation to a common central axis 50, so that the respective coupler elements 8, 10 can be embodied as rotationally symmetrical thus facilitating the connection.

FIG. 3 is a perspective view of a further embodiment of the first transmission element 12b and the second transmission element 18b of the coupler 6 as shown in FIG. 1. Here, the two transmission elements 12b, 18b each have a meandering shape, i.e., the U-shaped curves 37, which each determine the line profile 36 of one of the two transmission elements 12b, 18b, are not continuous and concatenated with the same direction of curvature but alternate the direction of curvature and at the same time are each spaced apart from one another by straight sections 52. As in the example embodiment shown in FIG. 2, here, the two transmission elements 12b, 18b each lie in one plane 54a, 54b so that the surfaces of the coupler elements 8, 10 in the respective region are also planar and formed by the respective dielectric substrate.

Figure 4:
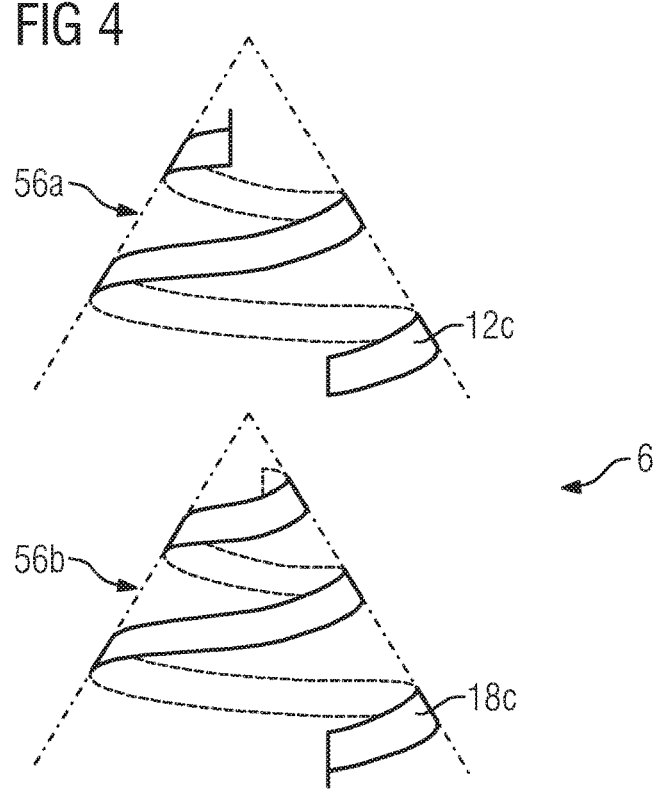

FIG. 4 is a side view of a further embodiment of the transmission elements 12c, 18c of a coupler 6. In the present case, the two transmission elements 12c, 18c are embodied as locally strip-shaped and each wound up with the same aperture angle in a spiral shape along outer cone surfaces 56a, 56b that are axially displaced with respect to one another. Herein, the strips formed by the transmission elements 12c, 18c strips each extend along the cone surfaces 56a, 56b.

FIG. 5 is a side view of a similar embodiment, wherein the first transmission element 12d and the second transmission element 18d are each embodied as locally strip-shaped and each wound up along coaxial outer surfaces of cylinders 58a, 58b. Herein, the strips formed by the transmission elements 12d, 18d each extend along the outer surfaces of the cylinders 58a, 58b.

In the embodiments shown in FIG. 4 and FIG. 5, the respective first coupler element 8 can in each case be embodied as a type of sleeve, into which the second coupler element 10 should preferably be introduced in a positive manner for the intended signal transmission.

Although the invention was illustrated and described in more detail by the preferred example embodiment, the invention is not restricted by this example embodiment. Other variations can be derived herefrom from the person skilled in the art without departing from the scope of protect The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an eleent is expressly recited using the phrase "means for" or, in the case f a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A coupler for contactless signal transmission, comprising:
   a first coupler element including a first transmission element; and
   a second coupler element including a second transmission element, a first signal contact for connection to a signal conductor being arranged on a first end of the first transmission element and a second signal contact for connection to a signal conductor being arranged on a first end of the second transmission element, wherein the first transmission element and the second transmission element each extend along mutually complementary surfaces of revolution,
   the first transmission element being configured to form a plurality of first U-shaped curves between the first end and a second end and in doing so forms a spiral or is wound around a lateral surface of a cylinder, the second transmission element being configured to form a plurality of second U-shaped curves between the first end and a second end and in doing so forms a spiral or is wound around a lateral surface of a cylinder, the first transmission element being configured, in operation, to transmit a signal supplied at the first signal contact to the second transmission element via directional coupling and the second transmission element being configured, in operation, to receive the signal from the first transmission element and output the signal via the second signal contact.

2. The coupler of claim 1, wherein the first coupler element is embodied as rotationally symmetrical and the second coupler element is embodied as complementary to the first coupler element.

3. The coupler of claim 1, wherein at least one of the first transmission element and the second transmission element, at least in sections, is embodied as locally flat.

4. The coupler of claim 1, wherein the first transmission element is applied to a dielectric substrate that forms a surface of the first coupler element.

5. The coupler of claim 1, wherein a first coil for inductive energy transmission is arranged in the first coupler element,
wherein a second coil for inductive energy transmission is arranged in the second coupler element and
wherein the first coil and the second coil are configured, when the coupler is in operation, to transmit energy at least one of
from the first coupler element to the second coupler element and
from the second coupler element to the first coupler element.

6. The coupler of claim 1, wherein the first coupler element and the second coupler element each include an electromagnetic absorber.

7. The coupler of claim 1, wherein the coupler is configured for the transmission of signals in a frequency range of from 200 MHz to 4 GHz.

8. A magnetic resonance imaging system comprising:
a local coil; and
the coupler of claim 1, wherein the first coupler element of the coupler is arranged on the local coil.

9. The coupler of claim 2, wherein the first coupler element and the second coupler element each include an electromagnetic absorber.

10. The coupler of claim 2, wherein the coupler is configured for the transmission of signals in a frequency range of from 200 MHz to 4 GHz.

11. A magnetic resonance imaging system comprising:
a local coil; and
the coupler of claim 2, wherein the first coupler element of the coupler is arranged on the local coil.

12. The coupler of claim 2, wherein a first coil for inductive energy transmission is arranged in the first coupler element,
wherein a second coil for inductive energy transmission is arranged in the second coupler element and
wherein the first coil and the second coil are configured, when the coupler is in operation, to transmit energy at least one of
from the first coupler element to the second coupler element and
from the second coupler element to the first coupler element.

* * * * *